(12) United States Patent
Photiadis et al.

(10) Patent No.: US 11,950,995 B2
(45) Date of Patent: *Apr. 9, 2024

(54) BIOARTIFICIAL PANCREAS

(71) Applicant: ISLA Technologies, Inc., San Carlos, CA (US)

(72) Inventors: Sara Joan Photiadis, San Francisco, CA (US); Douglas Marc Photiadis, Alexandria, VA (US); Thomas A. Kramer, San Carlos, CA (US)

(73) Assignee: ISLA Technologies, Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/193,959

(22) Filed: Mar. 31, 2023

(65) Prior Publication Data
US 2023/0248505 A1 Aug. 10, 2023

Related U.S. Application Data

(63) Continuation of application No. 17/981,287, filed on Nov. 4, 2022, now Pat. No. 11,642,212, which is a
(Continued)

(51) Int. Cl.
*A61K 9/00* (2006.01)
*A61F 2/02* (2006.01)
(Continued)

(52) U.S. Cl.
CPC .............. *A61F 2/022* (2013.01); *A61F 2/07* (2013.01); *A61F 2/90* (2013.01); *A61K 35/39* (2013.01);
(Continued)

(58) Field of Classification Search
CPC ...................................................... A61F 2/022
See application file for complete search history.

(56) References Cited

U.S. PATENT DOCUMENTS 4,323,457 A 4/1982 Sun et al.
4,355,426 A 10/1982 MacGregor
(Continued)

FOREIGN PATENT DOCUMENTS

DE 0439468 A1 6/1992
WO WO 83/03536 A1 10/1983
(Continued)

OTHER PUBLICATIONS

Bower, An Engineered microencapsulation membrane releasing FTY820 to precondition pancreatic islet transplantation, J Biomed Mater Res B Appl Biomater, 2018, 106(2), 555-568. (Year: 2018).
(Continued)

*Primary Examiner* — Paul W Dickinson
(74) *Attorney, Agent, or Firm* — Knobbe Martens Olson & Bear LLP

(57) ABSTRACT

A bioartificial device, such as a bioartificial pancreas, for implantation in a patient's vascular system. The bioartificial pancreas includes a scaffold adapted to engage an interior wall of a blood vessel, a cellular complex support by the scaffold and extending longitudinally within the interior cavity of the scaffold so as to be exposed to the blood flow when the scaffold is engaged with the blood vessel, the cellular complex support comprising one or more pockets bordered by thin film; and cellular complex comprising pancreatic islets disposed in the one or more pockets, the thin film being adapted to permit oxygen and glucose to diffuse from flowing blood into the one or more pockets at a rate sufficient to support the viability of the islets. The invention also includes methods of making and using a bioartificial pancreas.

20 Claims, 10 Drawing Sheets

Related U.S. Application Data continuation of application No. 17/697,692, filed on Mar. 17, 2022, now Pat. No. 11,517,416, which is a continuation of application No. PCT/US2020/052432, filed on Sep. 24, 2020.

(60) Provisional application No. 62/907,434, filed on Sep. 27, 2019.

(51) Int. Cl.

| | |
|---|---|
| *A61F 2/07* | (2013.01) |
| *A61F 2/90* | (2013.01) |
| *A61K 35/39* | (2015.01) |
| *A61L 27/56* | (2006.01) |
| *A61L 31/00* | (2006.01) |
| *A61L 31/08* | (2006.01) |
| *C12N 5/071* | (2010.01) |

(52) U.S. Cl.
CPC ............ *A61L 27/56* (2013.01); *A61L 31/005* (2013.01); *A61L 31/08* (2013.01); *C12N 5/0678* (2013.01); *A61F 2210/0004* (2013.01); *A61F 2210/0076* (2013.01); *A61F 2220/0075* (2013.01); *A61F 2240/002* (2013.01); *A61F 2250/0067* (2013.01); *A61L 2300/608* (2013.01); *A61L 2300/64* (2013.01); *A61L 2420/08* (2013.01); *C12N 2513/00* (2013.01)

(56) References Cited

U.S. PATENT DOCUMENTS

| | | | |
|---|---|---|---|
| 4,378,016 A | 3/1983 | Loeb | |
| 4,402,694 A | 9/1983 | Ash et al. | |
| 4,578,191 A | 3/1986 | Jaffrin et al. | |
| 4,689,293 A | 8/1987 | Goosen et al. | |
| 4,911,717 A | 3/1990 | Gaskill | |
| 4,997,443 A | 3/1991 | Walthall | |
| 5,002,661 A | 3/1991 | Chick et al. | |
| 5,116,494 A | 5/1992 | Chick et al. | |
| 5,182,111 A | 1/1993 | Aebischer et al. | |
| 5,262,055 A | 11/1993 | Bae et al. | |
| 5,314,471 A | 5/1994 | Bauker et al. | |
| 5,387,237 A | 2/1995 | Fournier et al. | |
| 5,453,278 A | 9/1995 | Chan et al. | |
| 5,534,025 A | 7/1996 | Moussy | |
| 5,626,561 A | 5/1997 | Butler et al. | |
| 5,674,289 A | 10/1997 | Fournier et al. | |
| 5,702,444 A | 12/1997 | Struthers et al. | |
| 5,704,910 A | 1/1998 | Humes | |
| 5,733,336 A | 3/1998 | Neuenfeldt et al. | |
| 5,741,334 A | 4/1998 | Mullon et al. | |
| 5,843,069 A | 12/1998 | Butler et al. | |
| 5,855,613 A | 1/1999 | Antanavich et al. | |
| 6,206,914 B1 | 3/2001 | Soykan et al. | |
| 6,582,955 B2 | 6/2003 | Martinez et al. | |
| 6,905,700 B2 | 6/2005 | Won et al. | |
| 7,044,965 B1 | 5/2006 | Spielberg | |
| 7,294,409 B2 | 11/2007 | Lye et al. | |
| 7,651,696 B2 | 1/2010 | Bates | |
| 7,713,544 B2 | 5/2010 | Chalkof et al. | |
| 7,713,573 B2 | 5/2010 | Owens et al. | |
| 7,955,613 B2 | 6/2011 | Bruce et al. | |
| 8,124,166 B2 | 2/2012 | Owens et al. | |
| 8,361,489 B2 | 1/2013 | Kennedy et al. | |
| 8,449,602 B2 | 5/2013 | Lye et al. | |
| 9,127,254 B2 | 9/2015 | Cohen et al. | |
| 9,770,349 B2 | 9/2017 | Owens et al. | |
| 9,788,978 B2 | 10/2017 | Rojo | |
| 10,034,963 B2 | 7/2018 | Hasilo et al. | |
| 2004/0258698 A1 | 12/2004 | Wightman et al. | |
| 2005/0255230 A1 | 11/2005 | Clerc et al. | |
| 2007/0173787 A1 | 7/2007 | Huang et al. | |
| 2008/0292690 A1 | 11/2008 | Wang | |
| 2012/0083767 A1 | 4/2012 | Gestenblith et al. | |
| 2014/0107280 A1 | 4/2014 | Luo et al. | |
| 2017/0157294 A1 | 6/2017 | Barkai et al. | |
| 2018/0085492 A1 | 3/2018 | Ameer et al. | |
| 2018/0098867 A1 | 4/2018 | Rojo | |

FOREIGN PATENT DOCUMENTS

| | | |
|---|---|---|
| WO | WO 1991/002498 A1 | 3/1991 |
| WO | WO 2005/102222 A2 | 11/2005 |
| WO | WO 2017/156026 A1 | 9/2017 |
| WO | WO 2018/017879 A1 | 1/2018 |
| WO | WO 2018/102077 A2 | 6/2018 |
| WO | WO 2018/209259 A1 | 11/2018 |
| WO | WO 2019/071135 A1 | 4/2019 |

OTHER PUBLICATIONS

Han, Edward X. et al., "Development of a Bioartificial Vascular Pancreas" Journal of Tissue Engineering, Jun. 2021, pp. 1-18, vol. 12.

Ikeda, Hideaki et al., "A Newly Developed Bioartificial Pancreas Successfully Controls Blood Glucose in Totally Pancreatectomized Diabetic Pigs" Tissue Engineering, 2006, pp. 1799-1802, vol. 12, No. 7.

Jeong, Metal stents placement for refractory pancreatic duct stricture in children, World J Gastroenterol, 2018, 24(3), 408-414 (Year: 2018).

Mikos, Antonios G. et al., "Mini-Review: Islet Transplantation to Create a Bioartificial Pancreas" Biotechnology and Bioengineering, 1994, pp. 673-677, vol. 43.

Prochorov, AV et al., "Treatment of insulin dependent diabetes mellitus with intravascular transplantation of pancreatic islet cells without immunosuppressive therapy", Advances in Medical Sciences, Jul. 2008, pp. 240-244, vol. 53, No. 2.

Wikipedia—"Surgical suture" Sep. 2019, Entire Document https://en.wikipedia.org/w/index.php?title=Surgical_suture&oldid=914015739.

International Search Report for PCT/US2020/052432 dated Mar. 1, 2021.

European Extended Search Report for EP 20870062.5 dated Oct. 5, 2023.

Growth of endothelial cell layer creating the "pocket"

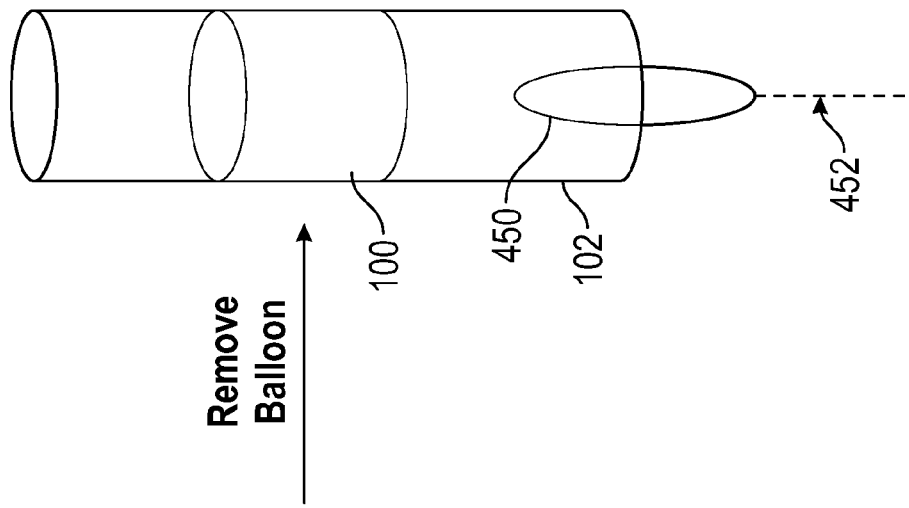
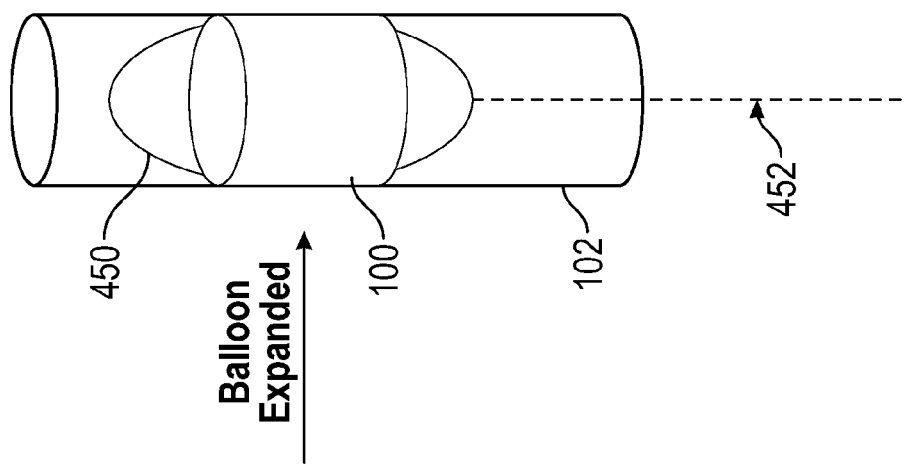
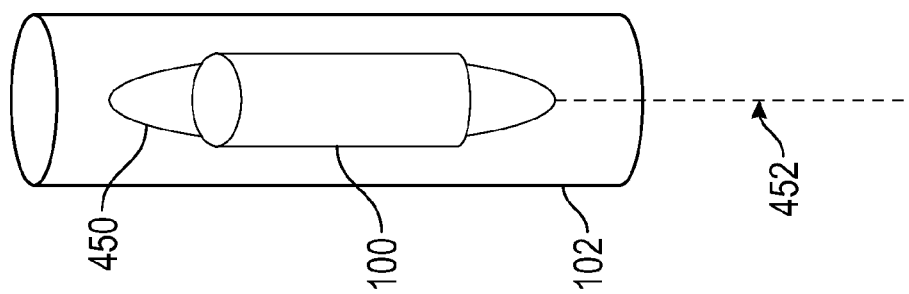

BIOARTIFICIAL PANCREAS

INCORPORATION BY REFERENCE TO ANY PRIORITY APPLICATIONS

This application is a continuation of U.S. application Ser. No. 17/981,287, filed Nov. 4, 2022, which itself is a continuation of U.S. application Ser. No. 17/697,692, issued as U.S. Pat. No. 11,517,416 filed Mar. 17, 2022, which is a continuation of PCT Application No. PCT/US2020/052432, filed Sep. 24, 2020, which claims the benefit of Provisional Application No. 62/907,434, filed Sep. 27, 2019. The entire contents of each of the above-referenced patent applications are expressly incorporated herein by reference.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND OF THE INVENTION

Field of the Invention

Described herein are intravascular bioartificial devices having a tubular geometry. In particular embodiments, the intravascular bioartificial device is bio-absorbable and includes a cellular complex of cells and a biocompatible material. In some embodiments, the cells are within pancreatic islets.

Description of the Related Art

Type 1 diabetes is a chronic metabolic disorder characterized by the body's inability to produce adequate amounts of insulin for regulating blood sugar. Type 1 diabetes accounts for roughly 10% of the greater than 420 million global cases of diabetes. Although the cause of type 1 diabetes is unknown, it is believed that an underlying mechanism involves autoimmune destruction of insulin-producing beta cells in the pancreas. If left untreated, complications related to high blood sugar can include damage to blood vessels, nerves and organs, seizures, diabetic ketoacidosis, and even death. Thus, people with Type 1 diabetes are traditionally insulin-dependent for life. Insulin treatment typically involves the use of syringes or insulin pumps to deliver insulin intravenously. However, daily insulin treatments are not always able to precisely and continuously meet the demands of the uncontrolled variations in stress, food intake, and physical activity levels.

Alternative treatments include pancreatic islet transplantation as a way to reduce the rigorous blood glucose monitoring and provide a more reliable means for generating and delivering insulin. Recent advances have provided the development of the bioartificial pancreas, which generally involves encapsulation of pancreatic islets in a semi-permeable environment to allow oxygen and glucose to reach the cells within the islets and to remove insulin and waste products from the cells. Although various kinds of bioartificial pancreases have been developed, many of these approaches have been found to have limitations.

What is needed, therefore, is an improved bioartificial pancreas and methods of treating and managing diabetes and other metabolic disorders.

SUMMARY

Described herein are bioartificial implants, such as bioartificial pancreas implants, that can provide automatic and continuous regulation of hormones, such as insulin, for a patient. The term "bioartificial" refers to the implant being composed of both living and manufactured components. The implant can include a cellular complex, which includes a combination of living cells and one or more biocompatible materials for sustaining the viability of the cells. In some cases, the cells are dispersed within a matrix of the biocompatible material. The cells may be encapsulated within the biocompatible material so that the biocompatible material can act as a semi-permeable immune barrier. When implanted within the patient's body, the cells can produce one or more hormones to modulate the patient's endocrine system. For example, the cells may secrete insulin and/or glucagon for modulating blood glucose levels within the patient's blood. The cells participate in a feedback system with the body to regulate the glucose levels based on hormone levels in the blood stream.

According to some embodiments, the cellular complex can be formed into or loaded onto a tubular shaped structure, such as a stent. The size and shape of the tubular structure can be configured for insertion within the patient's blood vessel while the biocompatible material can maintain the viability of the cells. The tubular shaped implant may be expandable such that the implant can be inserted within the patient's blood vessel while in a collapsed state and expanded at a target location within the blood vessel. When deployed, an outer wall of the tubular shaped implant may be secured against the blood vessel wall. By placing the implant close to the patient's blood stream, the cells can receive adequate oxygenation and nutrient support, and hormones generated by the cells may quickly enter the patient's blood stream.

In some cases, the bioartificial implant is configured to promote formation of a layer of endothelial cells over the implant, which may also act as a semi-permeable immune barrier. The implant can become encased within a pocket between the layer of endothelial cells and the blood vessel wall, which also can serve to protect the cells from the patient's immune system.

The implant may optionally be made of one or more bio-absorbable (also referred to as bioresorbable) materials that gradually degrade and become absorbed in the body. For example, the stent may be composed of a bio-absorbable polymer or metal, and the biocompatible material that supports and sustains the viability of the cells may also be composed of a bio-absorbable polymer. Thus, once the cells deteriorate or no longer produce hormones, the implant can become absorbed by the patient's body, making it unnecessary to retrieve the implant from the patient's body. After the implant is absorbed and cleared from the body, one or more additional implants may be inserted into the patient as needed.

Any of the bioartificial implants described herein can be used to treat one or more diseases or conditions. In some cases, the implant is used to treat a patient suffering from a metabolic disorder, such as type 1 diabetes. However, use of the implants is not limited to treating any particular type of metabolic disorder or to metabolic disorders in general. For example, the implant can be composed of pancreatic islets which may generate insulin, glucagon, amylin, somatostatin, ghrelin, and/or pancreatic polypeptides in any combination and ratio. Alternatively or additionally, the implant can be composed of thyroid hormone producing cells, parathyroid producing cells, adrenal-hormone producing cells (e.g., cortisol). Alternatively or additionally, the implant can be composed of non-cellular particles composed of chemotherapeutics and biologic drugs.

According to some embodiments, a bioartificial pancreas implant for placement within a patient's blood vessel includes: a stent having an outer surface defining a diameter sufficiently small for placement within the patient's blood vessel and an inner surface defining a lumen for blood to flow therethrough; and a cellular complex covering at least a portion of the inner and outer surfaces of the stent, the cellular complex comprising pancreatic islet cells and one or more biocompatible materials for sustaining viability of the pancreatic islet cells. The stent can be a bio-absorbable stent. The stent can include a number of struts, wherein the cellular complex covers at least a portion of the struts. The pancreatic islet cells may be embedded within pores of a matrix of the one or more biocompatible materials. The pancreatic islet cells may be dispersed within a matrix of the one or more biocompatible materials. The one or more biocompatible materials may be bio-absorbable. The bio-absorbable stent can include a bio-absorbable material having a resorption rate ranging from about 3 months to about 3 years. The bio-absorbable stent may include a bio-absorbable polymer and/or a bio-absorbable metal. The cellular complex can include one or more external layers of biocompatible material to fully encapsulate the pancreatic islet cells. A tubular wall of the bio-absorbable stent may include one or more blood flow pathways for oxygenating the blood vessel and promoting neovascularization of the pancreatic islet cells. The tubular wall may include a number of struts separated by spaces, where the blood flow pathways correspond to the spaces between the struts. The implant can include one or more chemical agents such as a growth factor and/or an anticoagulant. The cellular complex may include from about 50,000 and one million pancreatic islet cells. The implant may be configured to promote growth of endothelial cells between the patient's blood stream and the implant. The implant may include a semipermeable membrane that surrounds the bio-absorbable stent, the cellular complex, and the cells, where the semipermeable membrane is configured to substantially prevent exposure of the pancreatic islet cells to the patient's immune response and to allow permeation of hormones, oxygen, nutrients, and waste products.

According to some embodiments, a bioartificial pancreas implant for placement within a patient's blood vessel includes: a bio-absorbable material having pancreatic islets dispersed therein and configured to sustain a viability of the pancreatic islets, wherein the islets are encapsulated within the bio-absorbable material, wherein the bio-absorbable material has a tubular shape including an outer surface configured to contact the patient's blood vessel and an inner surface defining a lumen for blood to flow therethrough. The tubular shaped bio-absorbable material may have a diameter substantially the same as an inner diameter of the patient's blood vessel. The tubular shaped bio-absorbable material may include wall having a mesh-like structure with a number of holes. The implant can be configured to promote growth of endothelial cells between the patient's blood stream and the bio-absorbable material. The pancreatic islet cells can be embedded within pores of a matrix of the bio-absorbable material. The bio-absorbable material can include one or more polymer materials. The bio-absorbable material may include one or more external layers of bio-absorbable material to fully encapsulate the pancreatic islets. A wall of the tubular shaped bio-absorbable material may include one or more blood flow pathways for oxygenating the blood vessel and promoting neovascularization of the pancreatic islets. The one or more blood flow pathways may include openings within the walls of the tubular shaped bio-absorbable material. The implant can have a concentration of pancreatic islets ranging from about 5% and about 99% by weight.

According to some embodiments, a method of forming a bioartificial pancreas implant includes: forming a cellular complex by mixing pancreatic islets with one or more biocompatible materials, the one or more biocompatible materials configured to sustain a viability of the pancreatic islets; and coating at least a portion of a stent (optionally, a bio-absorbable stent) with the cellular complex, wherein at least a portion of the pancreatic islets become encapsulated by the biocompatible material. The method can further include coating the cellular complex with one or more layers of the one or more biocompatible materials to fully encapsulate the islets. Coating the stent with the cellular complex may involve a liquid deposition process, an ultrasonic coating process, or a combination of liquid deposition and ultrasonic coating processes. The stent may include a tubular wall having a number of struts separated by spaces, where coating the stent includes covering at least a portion of the struts. A concentration of the pancreatic islets in the cellular complex ranges from about 5% and about 99%.

According to some embodiments, a method of treating a patient suffering from diabetes includes: inserting the implant into the patient's blood vessel, wherein the implant comprises a bio-absorbable stent covered with a cellular complex comprising pancreatic islets and one or more biocompatible materials for sustaining viability of the pancreatic islets, wherein the bio-absorbable stent is in a contracted state during the inserting; and expanding the bio-absorbable stent at a target location in the patient's blood vessel such that the implant contacts vessel walls of the blood vessel.

Another aspect of the invention provides a bioartificial pancreas with a scaffold adapted to engage an interior wall of a blood vessel, the scaffold having a blood flow lumen extending longitudinally through an interior cavity of the scaffold so as to permit blood flow therethrough when the scaffold is engaged with the blood vessel; a cellular complex support by the scaffold and extending longitudinally within the interior cavity of the scaffold so as to be exposed to the blood flow when the scaffold is engaged with the blood vessel, the cellular complex support having one or more pockets bordered by thin film; and cellular complex including but not limited to pancreatic islets disposed in the one or more pockets, the thin film being adapted to permit oxygen and glucose to diffuse from flowing blood into the one or more pockets at a rate sufficient to support the viability of the islets.

In some embodiments of the bioartificial pancreas according to this aspect, the cellular complex support has a thickness from 0.30 mm to 1.0 mm when loaded with the cellular complex. In some or all of these embodiments, the cellular complex support may also have an attachment region adjacent the one or more pockets, the cellular complex support being attached to the scaffold at the attachment region. In such embodiments, the bioartificial pancreas may also include a thermal bond between the attachment region and the scaffold attaching the cellular complex support to the scaffold, a suture attaching the cellular complex support to the scaffold, and/or a pressure bond between the attachment region and the scaffold attaching the cellular complex support to the scaffold. The cellular complex support may also include a plurality of attachment regions adjacent a plurality of pockets, with cellular complex including but not limited to pancreatic islets disposed in the one or more pockets each of the pockets.

In some or all of these embodiments, the cellular complex support has two microporous thin film layers. Each microporous layer may have, e.g., a plurality of pores each having a diameter less than 100 μm, and each microporous layer may have a thickness less than 0.1 mm.

In some or all of these embodiments, the cellular complex may have an islet density of 2.5% to 100%, e.g., 12% to 30%.

In some embodiments, the cellular complex support extends substantially around the interior cavity, and in some embodiments the cellular complex support extends only partially around the interior cavity.

In some embodiments, the scaffold is an expandable stent. In such embodiments the cellular complex support may be attached to struts of the expandable stent.

In some or all of these embodiments, the scaffold and cellular complex support have a delivery configuration with a first diameter and a deployed configuration with a second diameter greater than the first diameter, the bioartificial pancreas being adapted to be delivered in the delivery configuration by a catheter to an implantation site within the blood vessel and to be expanded to the deployed configuration outside of the catheter at the implantation site. In some or all of these embodiments, the scaffold may be bio-absorbable.

Yet another aspect of the invention provides a bioartificial pancreas including a scaffold adapted to engage an interior wall of a blood vessel, the scaffold having a blood flow lumen extending longitudinally through an interior cavity of the scaffold so as to permit blood flow therethrough when the scaffold is engaged with the blood vessel; a cellular complex support supported by the scaffold and extending longitudinally within the interior cavity of the scaffold so as to be exposed to the blood flow when the scaffold is engaged with the blood vessel, the cellular complex support having a plurality of sealed pockets and a plurality of attachment regions attached to the scaffold; and cellular complex with pancreatic islets disposed in the sealed pockets, the cellular complex support being adapted to permit oxygen and glucose to diffuse from flowing blood into the sealed pockets at a rate sufficient to support the viability of the islets. The cellular complex support may have a thickness from 0.30 mm to 1.0 mm when loaded with the cellular complex.

Embodiments of the bioartificial pancreas according to this aspect may also include a thermal bond between one or more of the attachment regions and the scaffold attaching the cellular complex support to the scaffold, one or more sutures attaching the cellular complex support to the scaffold, and/or a pressure bond between one or more of the attachment regions and the scaffold attaching the cellular complex support to the scaffold.

In some or all of these embodiments, the cellular complex support has two microporous thin film layers. Each microporous layer may have, e.g., a plurality of pores each having a diameter less than 100 μm, and each microporous layer may have a thickness less than 0.1 mm.

In some or all of these embodiments, the cellular complex may have an islet density of 2.5% to 100%, e.g., 12% to 30%.

In some embodiments, the cellular complex support extends substantially around the interior cavity, and in some embodiments the cellular complex support extends only partially around the interior cavity.

In some embodiments, the scaffold is an expandable stent. In such embodiments the cellular complex support may be attached to struts of the expandable stent.

In some or all of these embodiments, the scaffold and cellular complex support have a delivery configuration with a first diameter and a deployed configuration with a second diameter greater than the first diameter, the bioartificial pancreas being adapted to be delivered in the delivery configuration by a catheter to an implantation site within the blood vessel and to be expanded to the deployed configuration outside of the catheter at the implantation site. In some or all of these embodiments, the scaffold may be bio-absorbable.

Still another aspect of the invention provides a bioartificial pancreas including a scaffold adapted to engage an interior wall of a blood vessel, the scaffold having a blood flow lumen extending longitudinally through an interior cavity of the scaffold so as to permit blood flow therethrough when the scaffold is engaged with the blood vessel; a cellular complex support supported by the scaffold and extending longitudinally within the interior cavity of the scaffold so as to be exposed to the blood flow when the scaffold is engaged with the blood vessel, the cellular complex support having one or more pockets; and cellular complex with pancreatic islets disposed in the one or more pockets; wherein the cellular complex support has a thickness from 0.30 mm to 1.0 mm when loaded with the cellular complex.

In one embodiment, the cellular complex support also has an attachment region adjacent the one or more pockets, the cellular complex support being attached to the scaffold at the attachment region. In such embodiments, the bioartificial pancreas may also include a thermal bond between the attachment region and the scaffold attaching the cellular complex support to the scaffold, a suture attaching the cellular complex support to the scaffold, and/or a pressure bond between the attachment region and the scaffold attaching the cellular complex support to the scaffold. The cellular complex support may also include a plurality of attachment regions adjacent a plurality of pockets, with cellular complex including but not limited to pancreatic islets disposed in the one or more pockets each of the pockets.

In some or all of these embodiments, the cellular complex support has two microporous thin film layers. Each microporous layer may have, e.g., a plurality of pores each having a diameter less than 100 μm, and each microporous layer may have a thickness less than 0.1 mm.

In some or all of these embodiments, the cellular complex may have an islet density of 2.5% to 100%, e.g., 12% to 30%.

In some embodiments, the cellular complex support extends substantially around the interior cavity, and in some embodiments the cellular complex support extends only partially around the interior cavity.

In some embodiments, the scaffold is an expandable stent. In such embodiments the cellular complex support may be attached to struts of the expandable stent.

In some or all of these embodiments, the scaffold and cellular complex support have a delivery configuration with a first diameter and a deployed configuration with a second diameter greater than the first diameter, the bioartificial pancreas being adapted to be delivered in the delivery configuration by a catheter to an implantation site within the blood vessel and to be expanded to the deployed configuration outside of the catheter at the implantation site. In some or all of these embodiments, the scaffold may be bio-absorbable.

Yet another aspect of the invention provides a bioartificial pancreas including: a scaffold adapted to engage an interior wall of a blood vessel, the scaffold having a blood flow lumen extending longitudinally through an interior cavity of the scaffold so as to permit blood flow therethrough when the scaffold is engaged with the blood vessel; a cellular complex support with a thin film supported by the scaffold and extending longitudinally within the interior cavity of the scaffold so as to be exposed to the blood flow when the scaffold is engaged with the blood vessel, the cellular complex support comprising and one or more pockets bordered by two microporous thin film layers, the thin film layers having a thickness less than 0.1 mm and a plurality of pores each having a diameter less than 100 μm; and cellular complex with pancreatic islets disposed in the one or more pockets.

In some or all of these embodiments, the cellular complex support may also have an attachment region adjacent the one or more pockets, the cellular complex support being attached to the scaffold at the attachment region. In such embodiments, the bioartificial pancreas may also include a thermal bond between the attachment region and the scaffold attaching the cellular complex support to the scaffold, a suture attaching the cellular complex support to the scaffold, and/or a pressure bond between the attachment region and the scaffold attaching the cellular complex support to the scaffold. The cellular complex support may also include a plurality of attachment regions adjacent a plurality of pockets, with cellular complex including but not limited to pancreatic islets disposed in the one or more pockets each of the pockets.

In some or all of these embodiments, the cellular complex support has two microporous thin film layers. Each microporous layer may have, e.g., a plurality of pores each having a diameter less than 100 μm, and each microporous layer may have a thickness less than 0.1 mm.

In some or all of these embodiments, the cellular complex may have an islet density of 2.5% to 100%, e.g., 12% to 30%.

In some embodiments, the cellular complex support extends substantially around the interior cavity, and in some embodiments the cellular complex support extends only partially around the interior cavity.

In some embodiments, the scaffold is an expandable stent. In such embodiments the cellular complex support may be attached to struts of the expandable stent.

In some or all of these embodiments, the scaffold and cellular complex support have a delivery configuration with a first diameter and a deployed configuration with a second diameter greater than the first diameter, the bioartificial pancreas being adapted to be delivered in the delivery configuration by a catheter to an implantation site within the blood vessel and to be expanded to the deployed configuration outside of the catheter at the implantation site.

Another aspect of the invention provides a method of preparing a bioartificial pancreas, the bioartificial pancreas having a scaffold and a cellular complex support. Some embodiments of the method include the following steps: injecting cellular complex through an opening into a pocket of the cellular complex support, the cellular complex including pancreatic islets; and closing the opening.

In some embodiments, the injecting step includes the step of injecting the cellular complex through a tube extending through the opening. Some embodiments include the additional step of withdrawing the tube, e.g., by optionally withdrawing the tube while injecting the cellular complex.

Some embodiments include the step of attaching the cellular complex support to the scaffold, e.g., before or after the step of injecting cellular complex into the pocket of the cellular complex support.

In embodiments in which the cellular complex support also has a plurality of pockets and a plurality of attachment regions, the injecting step may also include the step of injecting cellular complex into the plurality of pockets, and the attaching step may include the step of attaching the attachment regions to the scaffold.

Yet another aspect of the invention provides a method of treating a patient suffering from diabetes. In some embodiments, the method includes the steps of: implanting a bioartificial pancreas at an implantation site in a blood vessel of the patient, the bioartificial pancreas having a cellular complex support and a cellular complex disposed within the cellular complex support, the cellular complex including pancreatic islets; permitting blood to flow from the blood vessel through the bioartificial pancreas; diffusing oxygen from the blood into the cellular complex to maintain a minimum oxygen concentration of 0.05 mM at the pancreatic islets; diffusing glucose from the blood into the cellular complex; generating insulin with the pancreatic islets in response to levels of glucose diffused from the blood into the cellular complex; and delivering insulin generated by the pancreatic islets to the blood. In some embodiments, the implanting step includes the step of delivering the bioartificial pancreas through a catheter to the implantation site in the blood vessel and expanding the bioartificial pancreas from a delivery configuration to a deployed configuration.

These and other features and advantages are described herein.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

FIG. 1A shows perspective view of a partial section view of the bioartificial implant in the blood vessel; and FIG. 1B shows an axial cross section view of the bioartificial implant in the blood vessel.

FIG. 3A shows a longitudinal section view of the bioartificial implant; and FIG. 3B shows an axial cross-sectional view of the bioartificial implant.

FIGS. 4A-4C illustrate a bioartificial implant being placed within a blood vessel using a balloon delivery system.

DETAILED DESCRIPTION OF THE PREFERRED EMBODIMENT

Disclosed herein are bioartificial implants, such as bioartificial pancreas implants, that may be implanted into a patient's body for releasing one or more hormones into the patient's blood stream and for modulating the patient's endocrine system. The implant can be placed into the blood vessel and reside adjacent to or become incorporated within the blood vessel wall. The implant can include living cells, such as pancreatic islets, which generate hormones. The proximity of the implant to the patient's blood stream can provide quick delivery of the hormone(s) to the patient's blood stream and provide good vascularization for the cells.

Figure 1A:
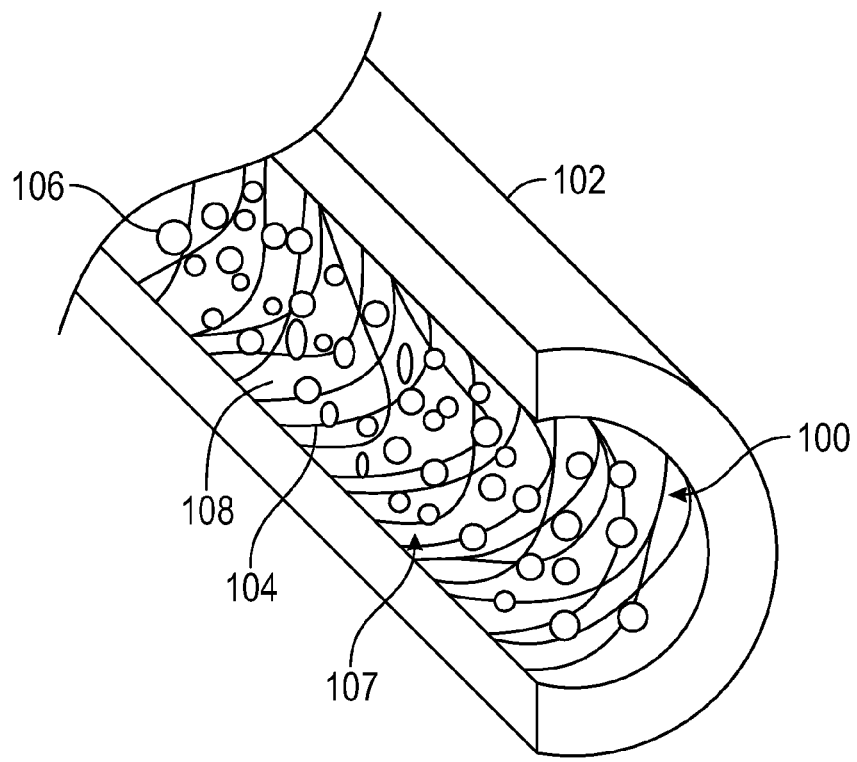
FIGS. 1A and 1B illustrate a bioartificial implant in a blood vessel.
Figure 1B:
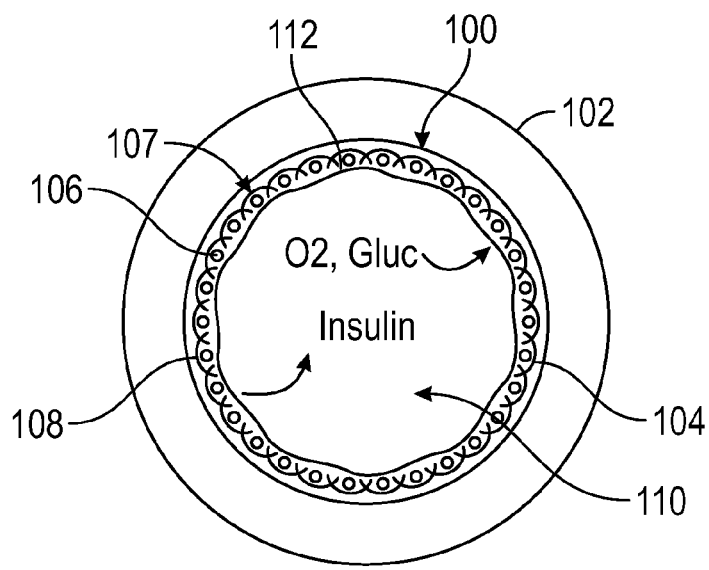

FIGS. 1A and 1B illustrate a bioartificial implant 100 within a blood vessel 102, according to some embodiments. The implant 100 can include a scaffold 104 (such as a stent) and a cellular complex 107 supported by the scaffold, which includes cells (such as pancreatic islets) and one or more biocompatible materials. When the implant is within a patient's blood vessel 102, glucose and oxygen from the flowing blood can reach the cellular complex 107, which can produce one or more hormones that may enter the patient's blood within the lumen 110 of the implant 100 and the blood vessel 102, thereby modulating the patient's endocrine system. In some cases, the implant 100 is used to treat a disease or condition, such as metabolic disorders including diabetes, in which case implant 100 is a bioartificial pancreas.

The cellular complex can be of any type. In some embodiments the cellular complex can include pancreatic islets such as adult human islets (either auto or allograft), xenogenic islets (e.g., porcine), embryonic beta cells, islet-like cells differentiated from stem cells, islet-like cells transdifferentiated from other tissue types including liver and pancreatic acinar cells and pancreatic ductal cells, genetically engineered and/or modified non-beta cells, or any combination thereof. In some cases, the cellular complex includes cell types other than pancreatic islets, such as thyroid hormone producing cells and/or adrenal hormone producing cells. The cellular complex may include a combination of pancreatic islets and other cell types. The type of cells may depend on the disease or condition and the treatment hormone(s) for treating such disease or condition. Different types of cells may be used to generate different type and/or amounts of hormones. In the case of islets, the cells may generate one or more of insulin, amylin, glucagon, somatostatin, ghrelin, and pancreatic polypeptides in any combination and ratio. In some embodiments, the cells are human cells, which may be obtained, for example, from a cell isolation laboratory. In some embodiments, the cells are animal cells, such as porcine cells. In some cases, the cells are genetically modified cells. In some cases, the implant includes stem cells.

The cellular complex may include cells be embedded within a matrix of biocompatible material, which can be configured to sustain the viability of the cells. The cells may be encapsulated by the biocompatible material. In some cases, as illustrated in FIG. 1B, the cellular complex 107 includes one or more external layers 112 of biocompatible material 108 to cover and substantially fully encapsulate the cells 106, thereby creating a barrier between the islet cells and the patient's immune response (e.g., lymphocytes, antibodies, macrophages and/or complementary molecules in the blood stream). The biocompatible material 108 may be semi-permeable to allow diffusion of nutrients (such as glucose) and/or oxygen across the biocompatible material 108 to reach the cells 106, and allow hormones and/or waste products from the cells 106 to diffuse across the biocompatible material 108 and out of the cellular complex 107. In some cases, the biocompatible material 108 may be infiltrated with one or more nutrients.

The biocompatible material 108 may be of porous material having a network of pores that contain the cells 106. Thus, the cells 106 may be dispersed within a matrix of the biocompatible material 108. In some cases, the cells 106 are in clusters within the matrix of biocompatible material 108. The biocompatible material 108 may be a bio-absorbable material, i.e., material that is configured to safely dissolve and/or be absorbed in the body. In some cases, the biocompatible material 108 includes an artificial and/or a natural polymer material. In particular embodiments, the biocompatible material 108 includes an alginate, a polyethylene glycol (PEG), an agarose, polytetrafluoroethylene (PTFE), or any combination thereof, and others. In some embodiments, the biocompatible material 108 include two or more different types of polymers.

The number and concentration of cells within the cellular complex 107 of the implant 100 may vary. In some embodiments, the cellular complex 107 includes from about 50,000 and one million cells (e.g., islets) (e.g., from about 50,000 to 100,000, from about 500,000 to one million, or from about 100,000 to about one million). In some embodiments, the concentration (by weight) of cells (e.g., islets) within the cellular complex 107 ranges from about 5% to about 100% (e.g., from about 5% to 99%, from about 5% to about 90%, from about 50% to about 90%, or from about 60% to about 80%).

The biocompatible material 108 may be any material that is not substantially harmful or toxic to living cells and/or tissue. The biocompatible material 108 may be configured to sustain the viability of the islets for a predetermined amount of time. In some instances, this predetermined amount of time may range from about 3 months to about 5 years (e.g., about 6 months to 2 years, about 3 months to 2 years, about 1 year to 3 years, or about 9 months to 2 years). According to some embodiments, the biocompatible material 108 includes one or more agents to help sustain the viability of the cells 106. For example, one or more enzymes and/or pH regulating agents may be infused or incorporated within the biocompatible material 108 to maintain a hospitable environment for the cells 106. In some cases, VEG-A and/or VEG-F is used to assist with neovascularization. The material 108 can include other cell types such as endothelial and mesenchymal stem cells. The material 108 can include extracellular matrix components such as collagen, elastin, fibronectin, laminin, and/or proteoglycans. The material 108 may include oxygen radical scavengers and/or oxygen carrying molecules.

The scaffold 104 can have a generally tubular shaped wall with an outer surface defining an outer diameter sufficiently small for residing within the blood vessel 102 and an inner surface defining a lumen 110 for blood to flow through once the stent is deployed within the vessel 102. For instance, the scaffold 104 wall may include a network of struts separated by spaces. The struts may be wires or threads that form a mesh or web-like structure with openings (also referred to as spaces or holes) between the wires or threads. The scaffold 104 supports the cellular complex 107 (cells 106 and biocompatible material 108). For example, at least a portion of the inner surface of the scaffold 104 may be covered with the cellular matrix 107. In some cases, at least a portion of the outer surface of the scaffold 104 is also (or alternatively) covered with the cellular matrix. In embodiments in which the scaffold has struts, the cellular matrix 107 may cover at least a portion of the struts of the scaffold 104. In some cases, the scaffold 104 is designed to be radially collapsible and/or expandable.

In some embodiments, the cellular complex 107 covers the scaffold 104 such that the cellular complex 107 partially or substantially fully occludes some or all of the openings in the scaffold 104 (e.g., between the struts of a stent). In cases in which at least a portion of the openings between the struts of the scaffold 104 are left open, these openings may act as pathways within the walls of the implant 100 to improve oxygenation of the cells 106 and/or blood vessel 102. In some embodiments, the openings in the scaffold 104 range in size from about 0.5 square millimeters ($mm^2$) and 25 $mm^2$ (e.g., about 1 to 5 $mm^2$, about 5 to 25 $mm^2$, or about 0.5 to 20 $mm^2$) in area along the walls of the implant 100. The walls of the implant 100 may include one or more different openings that act as blood flow paths. These additional or alternative blood flow openings may range in size from 100 $\mu m^2$ and 10,000 $\mu m^2$ (e.g., about 144 to 10,000 $\mu m^2$, about 1,000 to 5,000 $\mu m^2$, or about 500 to 9,000 $\mu m^2$) along the walls of the implant 100.

The scaffold 104 can be made of any suitable material. In some embodiments, the scaffold includes one or more bio-absorbable materials that is/are configured to dissolve and/or be absorbed in the body. In some embodiments, the bio-absorbable material of the scaffold 104 includes the same bio-absorbable material as the biocompatible material 108 of the cellular complex 107. In some embodiments, the bio-absorbable material of the scaffold 104 includes different materials compared to the biocompatible material 108 of the cellular complex 107. The bio-absorbable material of the scaffold 104 may include a polymer-based material, such as one or more of a polylactic acid polymer, a tyrosine poly carbonate polymer and a salicylic acid polymer. The bio-absorbable material of the stent 104 may include a metal-based material, such as one or more of iron, magnesium and zinc. The metal-based material may include one or more metal alloys.

In some variations, the implant 100 includes one or more materials that are not substantially bio-absorbable. For example, the scaffold 104 and/or the biocompatible material 108 may be composed of a material that that does not substantially degrade and/or become absorbed by the body. In such cases, the implant 100, or a portion thereof, may be configured to be retrieved from the patient's blood vessel. For instance, the implant 100 may be removed from the patient's body after the cells 106 are no longer producing sufficient amounts of hormones. In a particular embodiment, the biocompatible material 108 and cells 106 are bio-absorbable and the scaffold 104 is not substantially bio-absorbable (e.g., made of nitinol, titanium, stainless steel, and/or non-bio-absorbable polymer). Thus, once the biocompatible material 108 and cells 106 have been absorbed (or partially absorbed) by the body, the scaffold 104 may be retrieved using, for example, a retrieval catheter device. In some embodiments, the stent 104 is made of a non-bio-absorbable material.

If the scaffold 104 is made of a bio-absorbable material, the bio-absorbable material may be configured to dissolve and be absorbed in the body within a predetermined amount of time. The predetermined amount of time can vary depending on a number of factors such as the type of bio-absorbable material, the size of the scaffold 104 and/or the location of the implant 100 within the patient's body. In some embodiments, the resorption rate of the bio-absorbable material of the scaffold 104 may range from about 3 months to about 3 years (e.g., about 6 months to 2 years, about 3 months to 2 years, about 1 year to 3 years, or about 9 months to 2 years). In some embodiments, the bio-absorbable material of the scaffold 104 is configured to be absorbed in the body close to the time period in which the cells 106 no longer generate hormones. In some embodiments, the bio-absorbable material of the scaffold 104 is configured to be absorbed in the body for a period after the cells 106 no longer produce hormones. This may ensure that the bio-absorbable material of the scaffold 104 be present to support the cellular complex, including the cells 106, while they are generating hormones and at least up until they stop generating hormones. In some embodiments, the bio-absorbable material of the scaffold 104 is configured to be absorbed before the cells 106 are no longer generating hormones. For example, the cells 106 may continue to function within "the pocket" even after the scaffold 104 has been absorbed.

The implant 100 may be placed within any artery or vein of the patient's body. In some cases, a preferred location is within an artery so that the cellular complex can be exposed to oxygen-rich blood and nutrients. That is, arteries may have higher oxygen tension compared to that of veins. Further, the blood flow in an artery may confer a relatively immune-protected location in the body. Also, veins may have slower blood flow and lower pressure, making them possibly at higher risk for blood clots. However, an advantage of placing the implant in a vein is that the body may be able to form collateral venous pathways in case the vein becomes damaged.

In some embodiments, the blood vessel 102 may have a diameter of at least about 0.5 centimeters (cm). In some embodiments, the blood vessel may have a diameter ranging from about 0.5 cm to about 4 cm (e.g., about 0.5-3 cm, about 1-2 cm, about 1-3 cm, about 2-3 cm, about 1-4 cm, about 3-4 cm, about 1.5-3.5 cm, or about 2.5-4 cm).

According to some embodiments, the implant 100 is placed within an artery or a vein in or near the patient's pancreas, spleen, kidneys, liver, heart, and/or other organ. In some cases, the implant 100 is placed away from a particular organ, or away from organs in general. In some embodiments, one or more implants 100 may be deployed within one or more of the splenic artery, splenic vein, celiac artery, iliac artery, infra-renal aorta, thoracic aorta, abdominal aorta, carotid artery, hepatic artery, dorsal pancreatic artery, pancreatica magna artery, transverse pancreatic artery, anterior and posterior superior pancreatoduodenal artery, anterior and posterior inferior pancreatoduodenal artery, anterior and posterior superior pancreatoduodenal vein, and/or anterior and posterior inferior pancreatoduodenal vein. In some cases, the implant 100 is placed near or in the spleen since the spleen may be considered a non-essential organ. In some cases, the implant 100 placed in the splenic artery may provide some benefits since the splenic artery is relatively long, thereby allowing for deployment of multiple stents and/or a long stent. In some cases, placing the implant 100 in the infra-renal aorta provides some benefits because the infra-renal aorta may have a relatively large diameter, thereby allowing for a larger diameter stent to support a physiologic cell volume. Further, the femoral artery may provide relatively easy access to the infra-renal aorta with very minimal in-stent restenosis. In some embodiments, the implant 100 is placed in or near the iliac bifurcation, such as in the infrarenal aorta and/or the iliac arteries. In some cases, implantation at or near a bifurcation, such as the iliac bifurcation, may lower the likelihood of the implant 100 travelling within the blood vessel. Also, abdominal aorta and iliac arteries can have relatively large diameters that may experience little in-stent restenosis. Other considerations for placement of the implant 100 can include the likelihood of thrombus formation, the likelihood of an immune reaction, and the shape of the blood vessel (e.g., it may be more difficult to place the implant in winding blood vessel compared to straight blood vessels). In some cases, two or more implants 100 are placed within the patient's vascular system. For example, two or more implants 100 may be deployed within the same artery, different arteries, the same vein, different veins, or any combination of arteries and veins.

Once deployed in the patient's blood vessel 102, the implant 100 can be configured to contact the inner wall of the blood vessel 102. The outer surface of the implant 100 may have a diameter substantially the same as the inner diameter of the blood vessel 102. In some cases, the scaffold 104 may be configured to withstand the forces generated by the flow of blood. That is, blood can be allowed to flow through the lumen 110 of the scaffold 104 without the scaffold 104 collapsing. The scaffold 104 may be configured to withstand radial inward pressure exerted by the wall of the blood vessel 102 without collapsing. In some embodiments, the scaffold 104 can be configured to provide sufficient radial force to effectively increase a local diameter of the blood vessel lumen. This may enable the placement of a stent with an overall larger total diameter without occluding the lumen of the blood vessel 102.

In some cases, the scaffold 104 and the biocompatible material 108 may both be made of a continuous bio-absorbable material having a tubular shape with cells 106 dispersed therein. The walls of the tubular shaped bio-absorbable material may have a mesh or web-like structure with openings between struts of the mesh or web-like structure, which may act as blood flow paths for oxygenating the cells 106 and/or blood vessel 102, as described herein. In some cases, the walls of the tubular shaped bio-absorbable material have different openings instead of or in addition to the openings between struts as blood flow paths, as described herein. The walls of the tubular shaped bio-absorbable material may be configured to adhere to the inner walls of the blood vessel 102, thereby leaving the lumen 110 intact for blood to flow therethrough.

The implant 100 may be designed to operate within the range of temperatures expected to be encountered while implanted within the patient's body. That is, the implant can be nominally configured to operate around an average body temperature (e.g., about 37 degrees C.) and during body temperature fluctuations.

The size of the implant 100 may vary depending, for example, on the size of the blood vessel 102. In some embodiments, the implant 100 has a length ranging from about 2 centimeters (cm) and 10 cm (e.g., about 2-3 cm, about 3-10 cm, about 5-10 cm, or about 6-10 cm).

Figure 2A:
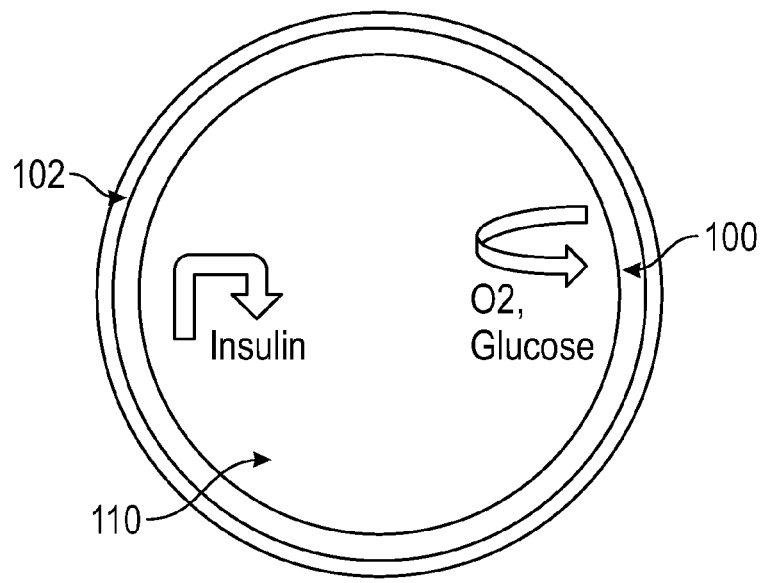
FIGS. 2A and 2B illustrate axial cross section views of a blood vessel undergoing re-endothelialization over a bioartificial implant.
Figure 2B:
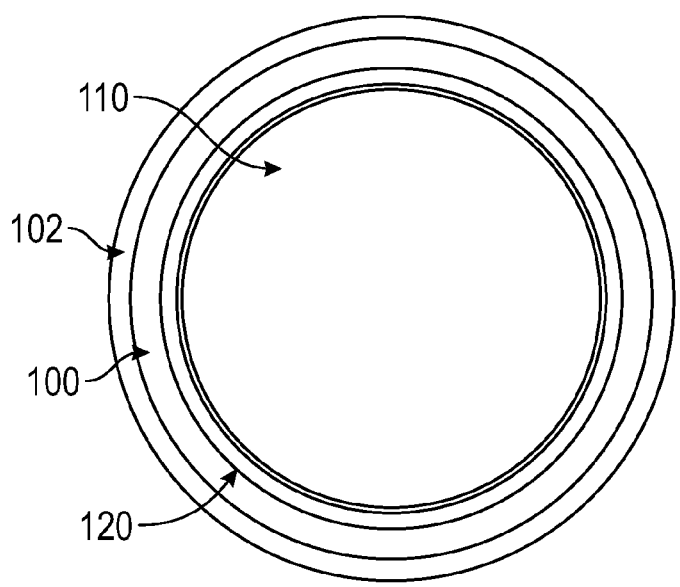

In some cases, an endothelial layer grows over the bio-artificial implant by a re-endothelialization process. FIGS. 2A and 2B illustrate an example of blood vessel wall 102 undergoing re-endothelialization over bioartificial implant 100, according to some embodiments. FIG. 2A shows the implant 100 implanted and functioning to secrete insulin within the lumen 110 of the implant 100 (and the blood vessel 102) in response to changes in blood glucose. After a period of time, an endothelial cell layer 120 may form over the implant 100, as shown in FIG. 2B. This re-endothelialization can create a space, or pocket, between the endothelial cell layer 120 and the blood vessel wall 102 for the implant 100 to reside. The cells of the implant 100 can continue to generate hormones (e.g., insulin) that is secreted into the lumen 110 while in the pocket. The endothelial layer 102 may act as a semi-permeable barrier that protects the cells 106 from the patient's immune response, and that allows diffusion of nutrients and/or oxygen to the islet cells 106 and hormones and/or waste from the cells 106. The endothelial layer 102 may be present with or without the one or more external layers 112 of biocompatible material 108 as described herein.

The bio-absorbable material of the implant 100 (e.g., scaffold 104 and/or biocompatible material 108) can gradually become absorbed by the body as the cells 106 continue to generate hormones (e.g., insulin). After a period of time, the cells 106 may no longer be able to generate hormones (e.g., insulin), which can be due to the biocompatible material 108 becoming absorbed by the body, the natural lifespan of the cells, or both. Once the implant becomes absorbed and the cells disintegrate and/or cease to secrete hormones (e.g., insulin) within the pocket, a new implant may be deployed within the blood vessel 102.

According to some embodiments, the bioartificial implant may be modified to include one or more chemical agents (e.g., small molecules, drugs, and/or proteins). For example, the implant 100 may include a growth factor, such as vascular endothelial growth factor (e.g., VEG-A and/or VEG-F) to promote growth of endothelial cells. The implant 100 may include an anticoagulant, such as heparin. Additional or alternative chemical agents can include anti-inflammatory drugs such as TNF alpha inhibitors and/or immune-suppression medications such as sirolimus or tacrolimus. The chemical agents may be coated onto or incorporated within the biocompatible material 108 of the cellular complex and/or the scaffold 104. According to some embodiments, the implant 100 can include one or more additional types of cells other than pancreatic islet cells. For example, follicular cells may be incorporated in the cellular complex 108 to release thyroid hormones (e.g., thyroid T4/T3) or other agents for modulating the endocrine system. The cellular complex 108 may include cells that produce parathyroid hormone (PTH) and/or adrenal gland hormones (e.g., cortisol and/or aldosterone) and/or sex hormones. In some cases, the implant 100 includes stem cells.

The implant may be delivered within the patient using any method. In some cases, the implant is delivered into the blood vessel using a catheterization procedure. As described herein, the implant can be collapsible and expandable. Thus, in some embodiments, the implant can be deployed intravascularly using endovascular techniques. One such technique involves a balloon delivery system.

Figure 3A:
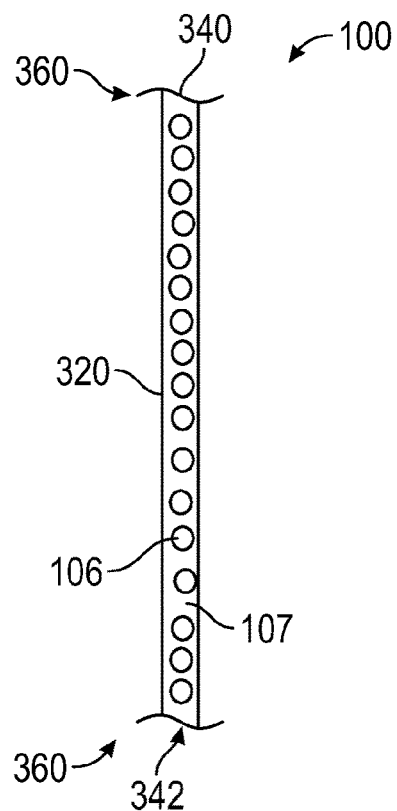
FIGS. 3A and 3B illustrate another variation of a bioartificial implant having one or more layers of a semipermeable membrane.
Figure 3B:
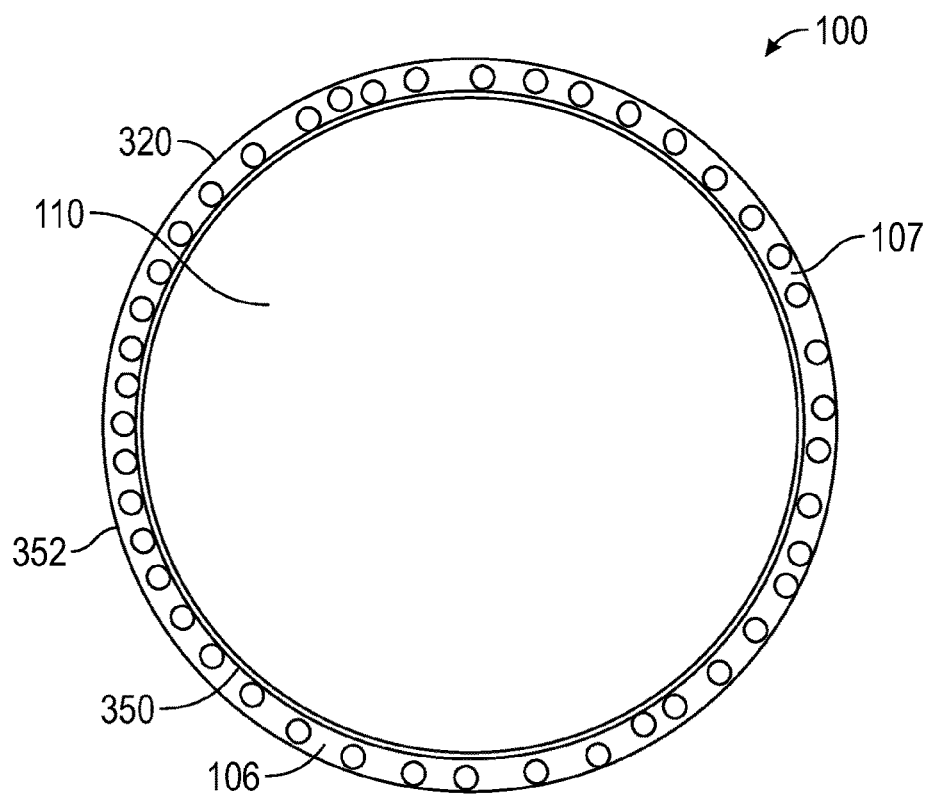

FIGS. 3A and 3B show a variation of the implant 100 where one or more layers of semipermeable material that surround the scaffold 104, the cellular complex 107, and the cells 106. FIG. 3A shows a longitudinal section view of the implant 100, and FIG. 3B shows an axial cross-sectional view of the implant 100. One or more layers 320 of a semipermeable membrane can be used to encase the scaffold 104 and the cellular complex 107. That is, the one or more layers 320 can cover an inner diameter 350 of the scaffold and the outer diameter 352 of the scaffold. The cellular complex 107 can be infused between the layer(s) 320. The layer(s) 320 of semipermeable membrane may be made of any biocompatible material that can substantially prevent exposure of the cells to the patient's immune response while also allowing permeation of hormones, oxygen, nutrients, and waste products to and from the cells in the cellular complex. In some embodiments, the layer(s) 320 of semipermeable membrane are made of a natural polymer and/or a synthetic polymer (e.g., PTFE). In some cases, the layer(s) 320 include two sheets of semipermeable material that are sealed together at a proximal end 340 and a distal end 342 of the implant 100. In some embodiments, the two sheets of semipermeable material are sealed together (e.g., via heat molding). In some embodiments, a sealant 360 is used to seal the two sheets of semipermeable material together. The sealant 360 may be made of any biocompatible material that can maintain a seal while within the patient's blood vessel. In some embodiments, the sealant 360 can be biocompatible glue and/or a biocompatible chemical sealant.

FIGS. 4A-4C illustrate an example of a bioartificial implant being placed within a blood vessel using a balloon delivery system. The balloon delivery system can include an inflatable balloon 450 and a guidewire 452. Before insertion into the blood vessel, the implant 100 can be mounted around the balloon 450 while the balloon 450 is in a deflated state and the stent of the implant 100 is in a collapsed state. The implant 100 may be manufactured on the balloon 450 or loaded onto the balloon 450 after manufacturing. FIG. 4A shows the balloon 450 with the implant 100 being guided through the lumen of the blood vessel 102 with the aid of the guidewire 452. The access site for insertion of the delivery system can vary depending on the target blood vessel and the target location within the target blood vessel. In some cases, the access site is an artery, such as a femoral or radial artery.

Once a target location within the blood vessel 102 is reached, the balloon 102 can be inflated so that it expands within the blood vessel 102, as shown in FIG. 4B. The expansion of the balloon 102 can cause the implant 100 to expand from its collapsed state to an expanded state and to contact the inner surfaces of the blood vessel 102. In some cases, the implant 100 is deployed to a fully expanded state, or nearly a fully expanded state. After the implant 100 is expanded, the balloon 450 can be deflated and removed from the vessel 102 using the guidewire 452.

In some embodiments, one or more radio-opaque markers may be used to visualize the delivery system and/or the implant 100 during delivery into the patient. For example, ring-shaped markers may be positioned at or near the ends of the implant 100 so that the doctor can view the markers using a radio frequency imaging techniques and deduce the location of the implant 100 during the procedure. The radio-opaque marker(s) may be removable from the delivery system and/or the implant 100 and the patient once the implant 100 is placed in the patient.

In other embodiments, the implant 100 is configured to be implanted within the blood vessel 102 without the use of a balloon. For example, the scaffold 104 (FIGS. 1A-3B) may be a self-expandable stent. In a particular variation, the self-expandable stent may be compressed within a delivery catheter and positioned within the blood vessel 102. An outer sheath of the delivery catheter can be retracted to allow the self-expandable stent to expand in a spring-like fashion to achieve a desired expansion diameter at the target location within the blood vessel 102.

Figure 5:
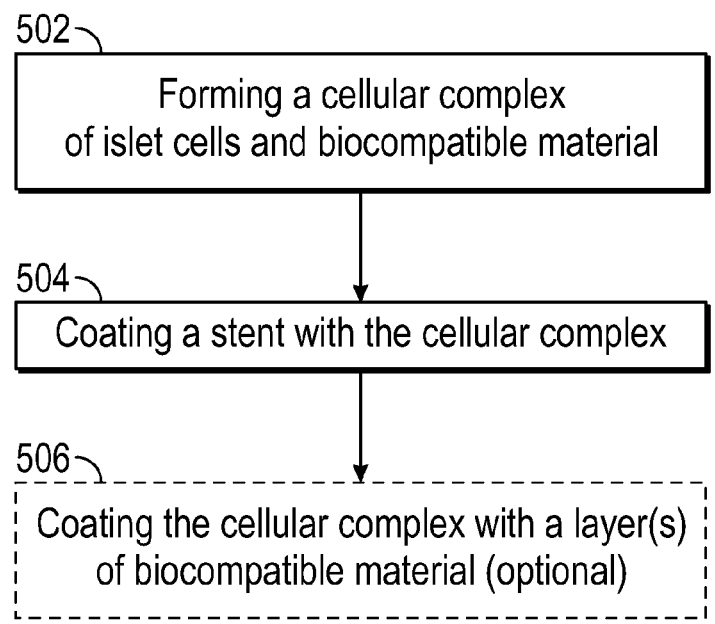
FIG. 5 illustrates a flowchart indicating a process for forming a bioartificial implant.

The bioartificial implants described herein can be manufactured using any of a number of different techniques. FIG. 5 illustrates a flowchart indicating a process for forming a bioartificial implant, according to some embodiments. A cellular complex can be formed (502), for example, by combining the cells with one or more biocompatible materials, which may also optionally be bio-absorbable. In particular embodiments, the biocompatible material may include an alginate, a PEG, an agarose, and/or a collagen polymer. The islet cells may be mixed with the biocompatible polymer(s) in a solution (e.g., aqueous solution) to form a slurry. In some embodiments, one or more chemical agents (e.g., drugs) and/or non-islet cells are added to the slurry to incorporate the chemical agents and/or non-islet cells into the cellular complex.

A scaffold that is designed to be inserted within a patient's blood vessel (e.g., a stent) can be coated with the cellular complex (504). The scaffold may be made of a bio-absorbable material and/or biocompatible material, such as a bio-absorbable polymer or metal stent. In some cases, the scaffold is pretreated with one or more chemical agents to promote adhesion of the cellular complex to the stent. Such agents may include one or more peptide coatings. For example, an integrin binding motif, such as the RGD motif (arginine-glycine-aspartic acid peptide), can be used to promote cellular adhesion to the scaffold. In some cases, one or more layers of biocompatible materials are used to coat the scaffold. In some embodiments, the scaffold includes one or more chemical agents (e.g., drugs) so that the scaffold may elute the chemical agent(s) while in the patient's body. The chemical agent(s) may be coated on the stent and/or incorporated within the material of the scaffold. Any of a number of coating methods may be used. In some embodiments, the cellular complex is deposited using a liquid deposition process, an ultrasonic coating process, a spray deposition process, or any combination thereof. In some embodiments, the cellular complex is deposited as a solution (e.g., aqueous solution). Once deposited, the solution with cellular complex may be allowed to dry to some degree. In some cases, the solution with cellular complex may be kept in solution (e.g., wet).

In some embodiments, the cellular complex on the scaffold may optionally be coated with one or more layers of biocompatible material (506). The biocompatible coating may serve to encapsulate the cells of the cellular complex from being eroded away from the scaffold due to exposure to flowing blood in the patient's blood stream while permitting oxygen and glucose to reach the cells and permitting waste products to leave the cells. Each of the layers of biocompatible coating may be very thin, e.g., ranging from about one nanometer to about one millimeter. The total thickness of the biocompatible coating may range from about one nanometer to about five millimeters.

FIGS. 6A-9 show an embodiment of a bioartificial pancreas 600. Cellular complex 602 made up of pancreatic islets and biocompatible material is disposed in pockets 604 of a cellular complex support 606. In embodiments, cellular complex 602 may have an islet density of 2.5% to 100%, or an islet density of 12% to 30%. In embodiments in which the islet density is less than 100%, the remainder of the cellular complex may be a porous medium, such as one or more of alginate, agarose, PEG, chitosan, etc.

To maintain the viability of the islets when the bioartificial pancreas is implanted within a blood vessel, and to enable the bioartificial pancreas to perform its function of releasing insulin in response to blood glucose levels, oxygen and glucose from the blood flowing through the device (and possibly from the vasa vasorum capillary network in the blood vessel wall) must reach the islets in the bioartificial pancreas. The higher the blood glucose level, the greater the oxygen consumption by the islets. The bioartificial pancreas implants of this invention therefore provide a structure than enables oxygen and glucose to diffuse from flowing blood into the cellular complex at a rate sufficient to support the viability of the islets. The devices also provide an islet density within the cellular complex no greater than that which can be supported by levels of oxygen reaching the islets and which can perform the function of supplying adequate amounts insulin in response to glucose reaching the islets within the cellular complex. In the embodiments described herein, oxygen reaches all of the islets in the cellular complex through the cellular complex support at a minimum concentration of 0.05 mM $O_2$.

Figure 6A:
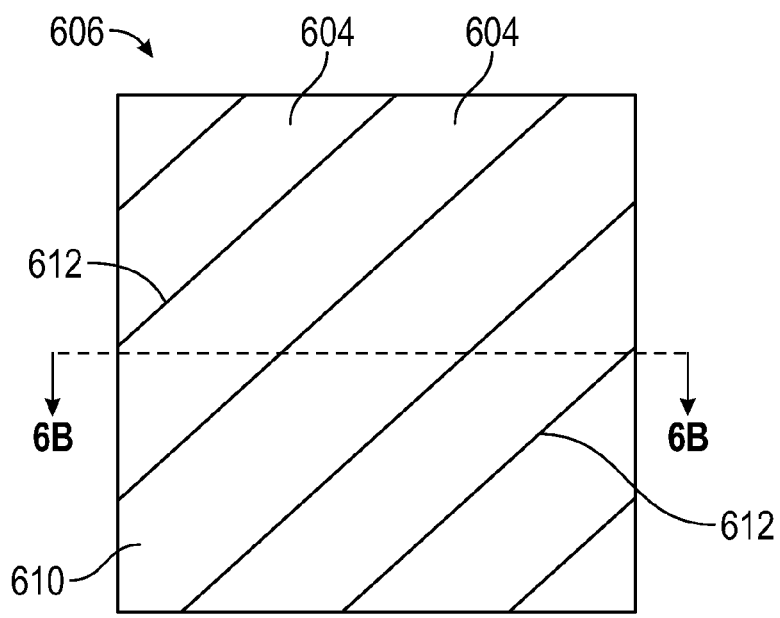
FIG. 6A shows an elevational view of a cellular complex support according to embodiments of the invention.
Figure 6B:
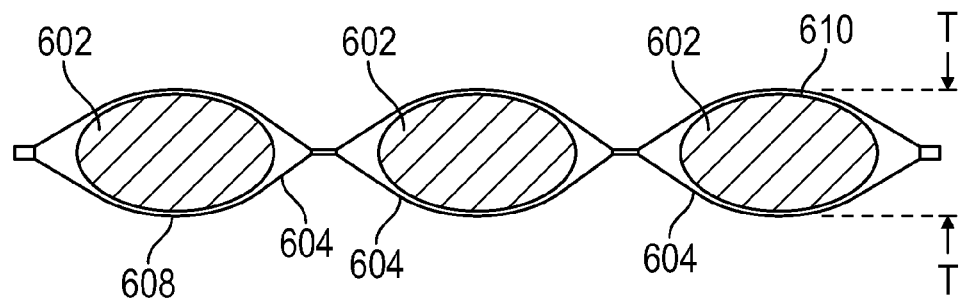
FIG. 6B shows a cross-section of the cellular complex support of FIG. 6A taken along the line 6B-6B in FIG. 6A.

In this embodiment, cellular complex support 606 has two layers 608 and 610 of a microporous thin film bordering the pockets 604. Layers 608 and 610 are attached to each other at the outer edges of cellular complex support 602 and in attachment regions 612 adjacent pockets 604. Cellular complex 602 is disposed in pockets 604. In embodiments, each layer of the thin film has a thickness less than 0.1 mm. In embodiments, the thin film layers can have pores with diameters less than 100 μm in order to enable glucose and oxygen in blood flowing through the scaffold to enter the pockets 604 to reach the cellular complex 602 at a rate sufficient to support the viability of the islets and to enable insulin produced by the islets in the cellular complex to reach the flowing blood. The pores may also permit glucose and/or oxygen to reach the cellular complex from vasa vasorum capillaries of the blood vessel in which the bioartificial pancreas 600 is implanted. Placement of the bioartificial pancreas in a blood vessel may result in angiogenesis of the vasa vasorum capillary network in that blood vessel. In embodiments, the thickness T of the assembled cellular complex support may be from 0.30 mm to 1.0 mm, inclusive, as shown in FIG. 6B.

Figure 7:
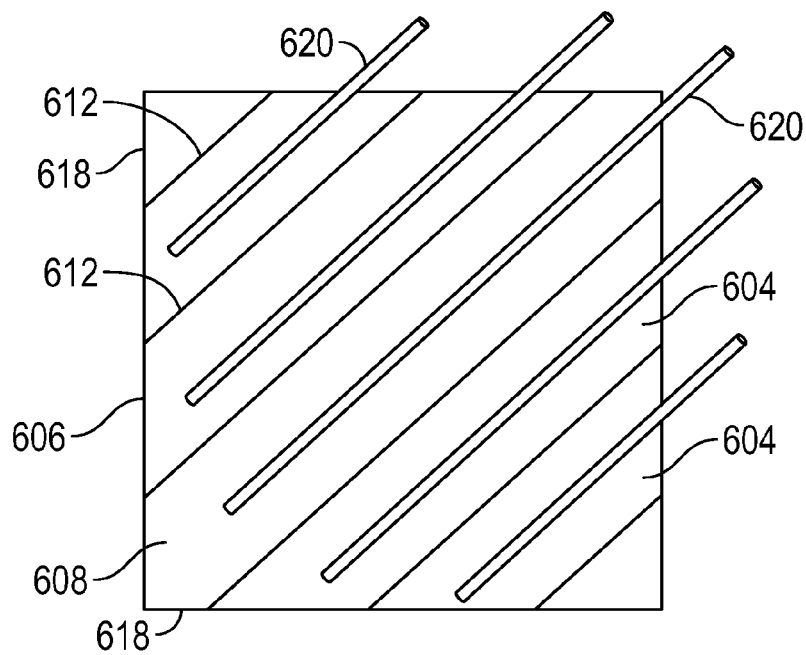
FIG. 7 shows an elevational view of a portion of the cellular complex support of FIG. 6A with filling tubes to be disposed within pockets of the cellular complex support.

In embodiments of the invention, the two layers 608 and 610 of cellular complex support 606 may be polymer, such as ePTFE, hydrophilic ePTFE, nylon, polyethylene or PEEK. To thermally bond the layers 608 and 610, a binding agent (e.g., FEP or polyurethane) may be applied to a top surface of layer 608 at the sites of the attachment regions 612 and around the outer edges 618 of layer 608. A small tube 620 (e.g., a 300-500 μm diameter polyethylene tube) may be placed on the top side of layer 608 at the sites of each pocket 604, with an open end of each tube 620 at one end of the pocket and a portion of each tube 620 extending beyond the border of layer 608, as shown in FIG. 7. A bottom side of the second layer 610 may then be placed on the top side of layer 608 and over the tubes 620. An oven or a sealing device may then be used to heat the layers and bonding agent (e.g., at 200° F.-500° F.) to thermally bond the layers to each other at the attachment regions 612 and the outer edges 618 of the cellular complex support 606.

Other embodiments forego the use of a binding agent and rely on a sufficiently low melting point of the polymer from which layers 608 and 610 are formed. Heat applied to the bottom surface of layer 608 and the top surface of layer 610 at the attachment regions 612 and/or outer edges 618 will melt the polymer locally. The polymer will then resolidify to form welds at the attachment regions 612 and/or edges 618.

In one optional preparation method for cellular complex 602 and cellular complex support 606, islets are mixed at 37° C. with a microporous hydrogel (e.g., alginate, fibrin, chitosan, agarose, polyethylene glycol) at an islet density of 12%-30%, and a polymer crosslinker is added to harden the hydrogel to provide greater mechanical stability for protection of the islets. A Hamilton syringe may be used to inject the cellular complex into pockets 604 via tubes 620. Each tube 620 may be slowly withdrawn from its pocket 604 as the cellular complex is injected to ensure even distribution of the cellular complex in the pocket. After cellular complex injection is complete and tubes 620 have been withdrawn from pockets 604, the outer edges of each pocket 604 may be heat sealed in the manner described above to close the pockets and to prevent the escape of any cellular complex. After sealing pockets 604, the cellular complex support may be cooled at room temperature (i.e., 4° C.). The cellular complex 602 may be injected into the cellular complex support 606 before or after attaching the cellular complex support to the scaffold.

Figure 8:
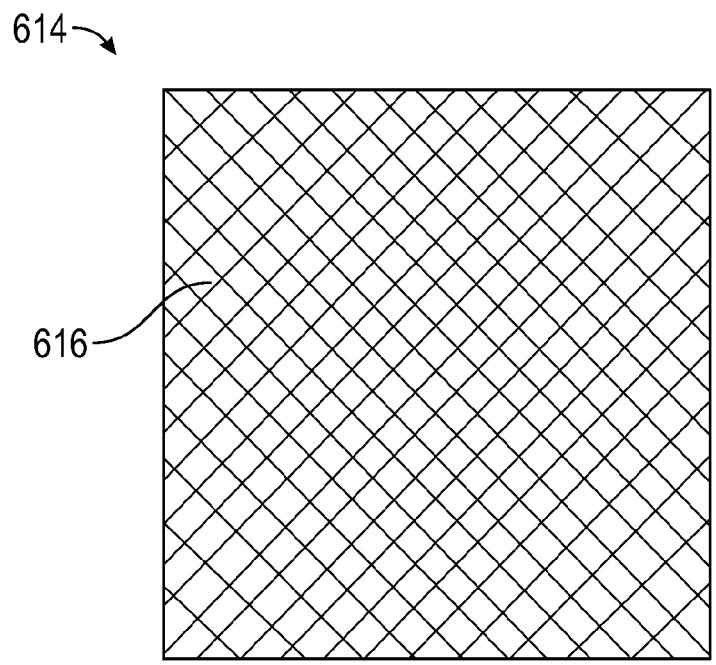
FIG. 8 shows a flat elevational view of a scaffold to which a cellular complex support may be attached.
Figure 9:
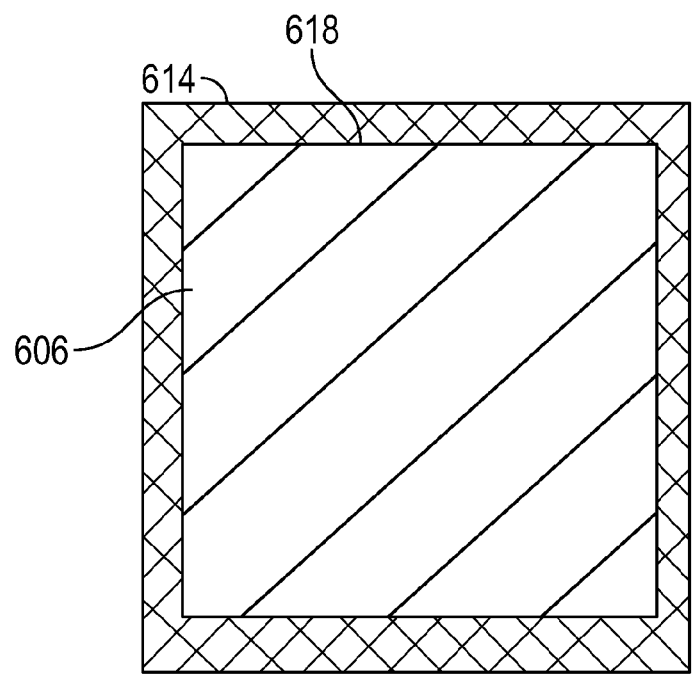
FIG. 9 shows a flat elevational view of the cellular complex support of FIG. 6A attached to the scaffold of FIG. 8.

The bioartificial pancreas 600 may be configured as a cylinder or portion of a cylinder so as to rest against the inner wall of a blood vessel, such as the descending aorta. FIGS. 8 and 9 show scaffold 614 and cellular complex support 606 in a flat configuration, however, for purposes of illustration. In this embodiment, scaffold 614 is a cylindrical mesh stent surrounding an internal cavity. Scaffold 614 may be formed from, e.g., a shape-memory alloy such as Nitinol, or it may be formed from a bio-absorbable material. Scaffold 614 can be compressed for delivery and expanded (e.g., by self-expansion) for deployment in a patient's blood vessel, such as the descending aorta. The attachment regions 612 and/or outer edges 618 of the cellular complex support 606 can be attached to the filaments 616 of the scaffold 614 via a thermal bond, pressure bond, sutures, glue, or any other suitable attachment mechanism. In this embodiment, the cellular complex support 606 substantially surrounds the entire inner cavity of the scaffold. In other embodiments, the cellular complex support borders only a portion of the interior cavity of the scaffold.

In embodiments, one or both of the thin film layers can have one or more of the following on outside surfaces: a hydrogel, heparin, growth factors (e.g., VEGF, VEGA), and immunotherapy substances (e.g., sirolimus, tacrolimus).

The bioartificial pancreas of this invention may be delivered via a catheter to the desired implantation site within a blood vessel, such as the infrarenal aorta. The bioartificial pancreas may have a smaller diameter delivery configuration and a larger diameter deployed configuration. The bioartificial pancreas may have a diameter of 1-10 mm in the delivery configuration and a diameter of 5 mm-25 mm in the deployed configuration.

Figure 10B:
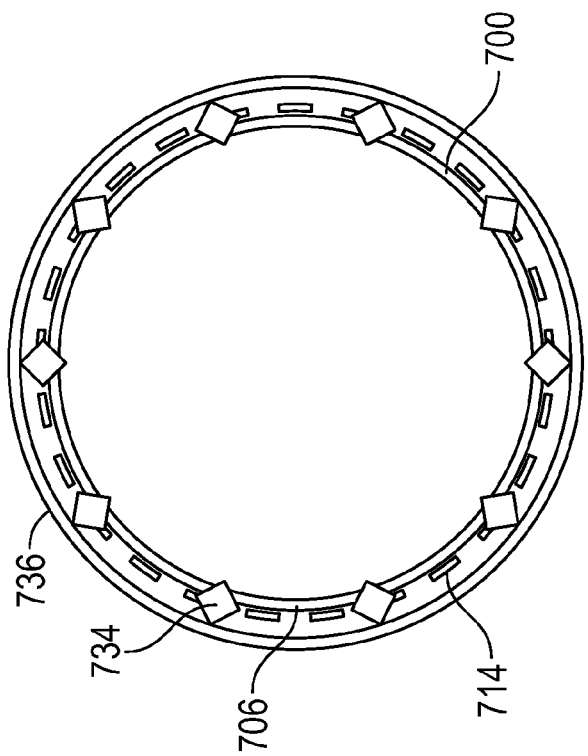
FIGS. 10A and 10B show end views of a bioartificial pancreas according to an embodiment of this invention in delivery and deployed configurations, respectively.
Figure 10A:
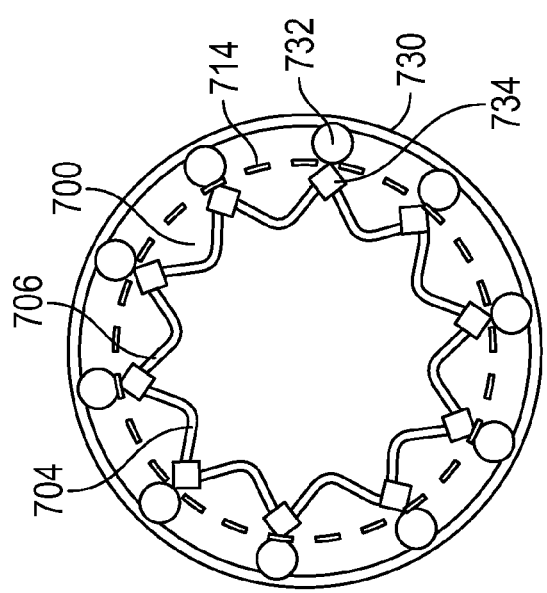

FIGS. 10A-B illustrate delivery and deployment configurations of a bioartificial pancreas 700 according to one embodiment of the invention. As in embodiments described above, bioartificial pancreas 700 has a cellular complex support 706 attached to a scaffold 714. Cellular complex, such as islets and a microporous hydrogel, as described above, is loaded into cellular complex support 706. As shown in FIG. 10A, the bioartificial pancreas 700 is loaded into a delivery catheter 730 in a smaller diameter delivery configuration such that the pockets 704 containing the cellular complex extend radially inward while the attachment regions 712 remain attached to scaffold 714. Protrusions 732 on the inner surface of catheter 730 engage outer surfaces of the scaffold 714, such as at scaffold struts 734. When the bioartificial pancreas 700 emerges from the distal end of the catheter at the desired implantation site in the blood vessel 736, scaffold 714 self-expands and pockets 704 move radially outward. FIGS. 10A-B are not necessarily drawn to scale.

Figure 11B:
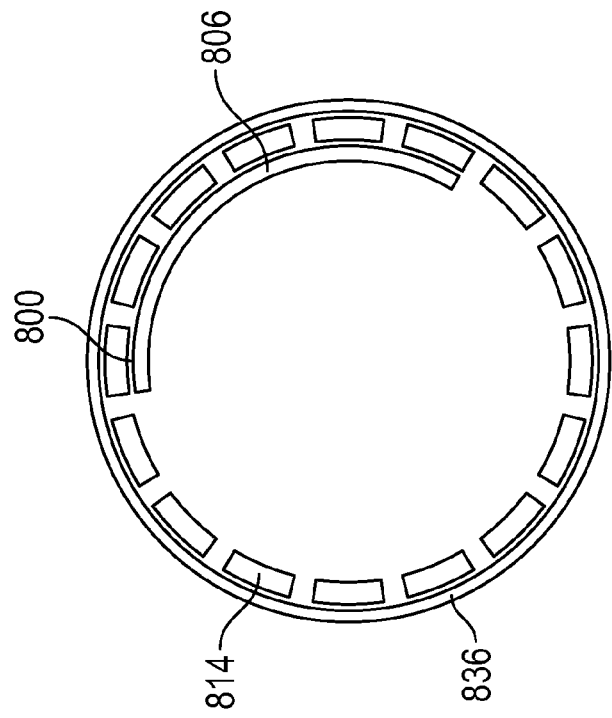
FIGS. 11A and 11B show end views of a bioartificial pancreas according to another embodiment of this invention in delivery and deployed configurations, respectively.
Figure 11A:
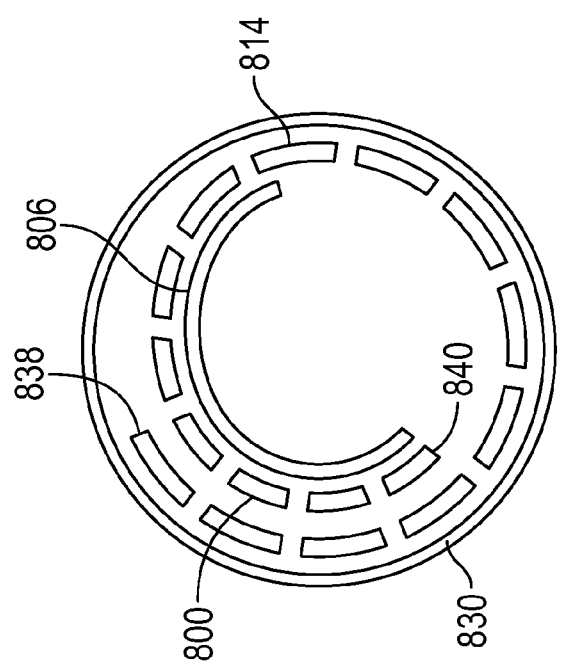

FIGS. 11A-B illustrate delivery and deployment configurations of a bioartificial pancreas 800 according to another embodiment of the invention. As in embodiments described above, bioartificial pancreas 800 has a cellular complex support 806 attached to a scaffold 814, and cellular complex, such as islets and a microporous hydrogel, as described above, is loaded into cellular complex support 806. In this embodiment, the cellular complex support 806 covers a smaller portion of the inside surface area of scaffold 814 compared to other embodiments, and instead of being a closed cylinder, the scaffold 814 has open edges 838 and 840. As shown in FIG. 11A, the bioartificial pancreas 800 is loaded into a delivery catheter 830 in a smaller diameter delivery configuration by rolling scaffold 814 into a spiral. When the bioartificial pancreas 800 emerges from the distal end of the catheter at the desired implantation site in the blood vessel 836, scaffold 814 self-expands by unwinding the spiral. FIG. 11B shows scaffold 816 unwound such that the open edges substantially meet. Depending on the diameter of blood vessel 836, however, the open edges 838 and 840 of scaffold 814 may be separated, forming an open cylinder or tube, or the open edges 838 and 840 may still overlap somewhat, forming part of a spiral. FIGS. 11A-B are not necessarily drawn to scale.

Figure 12A:
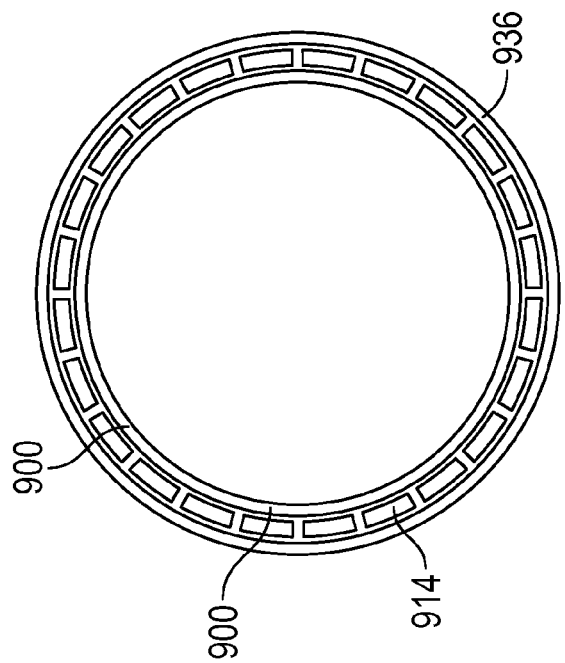
FIGS. 12A and 12B show end views of a bioartificial pancreas according to still another embodiment of this invention in delivery and deployed configurations, respectively.
Figure 12B:
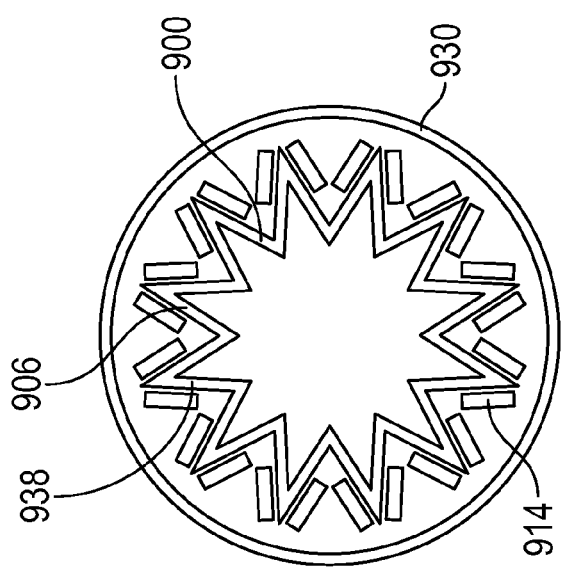

FIGS. 12A-B illustrate delivery and deployment configurations of a bioartificial pancreas 900 according to yet another embodiment of the invention. As in embodiments described above, bioartificial pancreas 900 has a cellular complex support 906 attached to a scaffold 914. Cellular complex, such as islets and a microporous hydrogel, as described above, is loaded into cellular complex support 906. As shown in FIG. 12A, the bioartificial pancreas 900 is loaded into a delivery catheter 930 in a smaller diameter delivery configuration such that the cellular complex support 906 and scaffold 914 form radially inward folding portions 938. When the bioartificial pancreas 900 emerges from the distal end of the catheter at the desired implantation site in the blood vessel 936, scaffold 914 self-expands to substantially eliminate folding portions 938, as shown in FIG. 12B. FIGS. 12A-B are not necessarily drawn to scale.

In some embodiments, the stent and/or the cellular complex is manufactured using a three-dimensional (3D) printing process. In some cases, the entire implant, including the stent and/or the cellular complex is manufactured using a 3D printing process.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A bioartificial implant system, the system comprising:
   a scaffold configured to engage an interior wall of a blood vessel of a subject, the scaffold comprising a lumen extending longitudinally through an interior cavity of the scaffold so as to permit blood flow therethrough when the scaffold is engaged with the blood vessel; and
   a cellular complex support supported by the scaffold and extending longitudinally within the interior cavity of the scaffold so as to be exposed to the blood flow when the scaffold is engaged with the blood vessel, the cellular complex support comprising
      one or more pockets and a plurality of attachment regions configured to attach to the scaffold, and
      at least one microporous thin film layer bordering the one or more pockets,
      the cellular complex support configured to receive a plurality of cells within the one or more pockets, and wherein the cellular complex support is configured to permit nutrients to diffuse from the blood flow into the one or more pockets.

2. The bioartificial implant system of claim 1, comprising the plurality of cells disposed in the one or more pockets.

3. The bioartificial implant system of claim 2, wherein the plurality of cells comprise stem cells.

4. The bioartificial implant system of claim 2, wherein the plurality of cells comprise pancreatic islets.

5. The bioartificial implant system of claim 1, wherein the cellular complex support has a thickness from 0.30 mm to 1.0 mm when loaded with a cellular complex.

6. The bioartificial implant system of claim 1, wherein the cellular complex support comprises an opening configured to accept a tube configured to inject cells into the cellular complex support.

7. The bioartificial implant system of claim 6, the opening configured to be sealed.

8. The bioartificial implant system of claim 1, the cellular complex support comprises a biocompatible material.

9. The bioartificial implant system of claim 1, the cellular complex support configured to receive a slurry, the slurry comprising the plurality of cells and a biocompatible material.

10. The bioartificial implant system of claim 1, wherein the cellular complex support is configured to attach to the scaffold after the plurality of cells are added to the cellular complex support.

11. The bioartificial implant system of claim 1, wherein the cellular complex support is configured to receive cells while attached to the scaffold.

12. The bioartificial implant system of claim 1, wherein the cellular complex support further comprises an attachment region adjacent to the one or more pockets, the cellular complex support being attached to the scaffold at the attachment region.

13. The bioartificial implant system of claim 12, further comprising a thermal bond between the attachment region and the scaffold attaching the cellular complex support to the scaffold.

14. The bioartificial implant system of claim 12, further comprising a pressure bond between the attachment region and the scaffold attaching the cellular complex support to the scaffold.

15. The bioartificial implant system of claim 1, further comprising a suture attaching the cellular complex support to the scaffold.

16. The bioartificial implant system of claim 1, wherein the plurality of attachment regions are adjacent to the one or more pockets, with the cellular complex support comprising islets being disposed in each pocket.

17. The bioartificial implant system of claim 1, wherein the at least one microporous thin film layer are configured to permit oxygen and glucose to diffuse to the plurality of cells within the one or more pockets.

18. The bioartificial implant system of claim 1, wherein each microporous thin film layer comprises a plurality of pores each having a diameter less than 100 µm.

19. The bioartificial implant system of claim 1, wherein each of the at least one microporous thin film layer has a thickness less than 0.1 mm.

20. The bioartificial implant system of claim 1, wherein the scaffold is an expandable stent.

\* \* \* \* \*